(12) United States Patent
Brannan (10) Patent No.: US 8,568,404 B2
(45) Date of Patent: Oct. 29, 2013

(54) BIPOLAR ELECTRODE PROBE FOR ABLATION MONITORING

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 716 days.

(21) Appl. No.: 12/708,974

(22) Filed: Feb. 19, 2010

(65) Prior Publication Data
US 2011/0208184 A1    Aug. 25, 2011

(51) Int. Cl.
*A61B 18/14* (2006.01)

(52) U.S. Cl.
USPC ............................................. 606/41; 606/34

(58) Field of Classification Search
USPC ...................................................... 606/34, 41
See application file for complete search history.

(56) References Cited

U.S. PATENT DOCUMENTS

| | | | |
|---|---|---|---|
| 4,204,549 A | 5/1980 | Paglione |
| 4,291,708 A | 9/1981 | Frei et al. |
| D263,020 S | 2/1982 | Rau, III |
| 4,402,309 A | 9/1983 | Harrison |
| 4,458,694 A | 7/1984 | Sollish et al. |
| 4,507,602 A | 3/1985 | Aguirre |
| 4,510,437 A | 4/1985 | Iskander |
| 4,539,640 A | 9/1985 | Fry et al. |
| 4,583,869 A | 4/1986 | Chive et al. |
| 4,729,385 A | 3/1988 | Juncosa et al. |
| D295,893 S | 5/1988 | Sharkany et al. |
| D295,894 S | 5/1988 | Sharkany et al. |
| 4,765,179 A | 8/1988 | Fuller et al. |
| 4,780,661 A | 10/1988 | Bolomey et al. |
| 4,798,215 A | 1/1989 | Turner |
| 4,805,621 A | 2/1989 | Heinze et al. |
| 5,025,810 A | 6/1991 | Kikuchi et al. |
| 5,033,478 A | 7/1991 | Kikuchi et al. |
| RE33,791 E | 1/1992 | Carr |
| 5,143,079 A | 9/1992 | Frei et al. |
| 5,148,814 A | 9/1992 | Kikuchi et al. |
| 5,227,730 A | 7/1993 | King et al. |
| 5,233,306 A | 8/1993 | Misra |
| 5,334,941 A | 8/1994 | King |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Michael Peffley
*Assistant Examiner* — Khadijeh Vahdat (57) ABSTRACT

An electromagnetic surgical ablation system having a generator adapted to selectively provide surgical ablation energy to an ablation probe, and methods of operating same, are disclosed. The system includes a controller operatively coupled to the generator, and at least one tissue sensor probe operatively coupled to the controller. The at least one tissue sensor provides a tissue impedance measurement to the controller. A sensor probe may be designated a threshold probe adapted to sense when tissue is sufficiently ablated, or, a critical structure probe adapted to protect an adjacent anatomical structure from undesired ablation. During an electromagnetic tissue ablation procedure, the controller monitors tissue impedance to determine tissue status, to activate an indicator associated therewith, and, additionally or alternatively, to activate and deactivate the generator accordingly.

11 Claims, 6 Drawing Sheets

(56) References Cited

U.S. PATENT DOCUMENTS

| | | |
|---|---|---|
| 5,344,435 A | 9/1994 | Turner et al. |
| 5,364,392 A | 11/1994 | Warner et al. |
| 5,385,148 A | 1/1995 | Lesh et al. |
| 5,452,716 A | 9/1995 | Clift |
| 5,502,394 A | 3/1996 | Piau |
| 5,503,150 A | 4/1996 | Evans |
| 5,508,203 A | 4/1996 | Fuller et al. |
| 5,531,676 A | 7/1996 | Edwards et al. |
| 5,540,684 A | 7/1996 | Hassler, Jr. |
| 5,549,639 A | 8/1996 | Ross |
| 5,571,147 A | 11/1996 | Sluijter et al. |
| 5,643,257 A | 7/1997 | Cohen et al. |
| 5,658,282 A | 8/1997 | Daw et al. |
| 5,713,942 A | 2/1998 | Stern et al. |
| 5,744,971 A | 4/1998 | Chan et al. |
| 5,776,176 A | 7/1998 | Rudie |
| 5,792,668 A | 8/1998 | Fuller et al. |
| 5,800,494 A | 9/1998 | Campbell et al. |
| 5,810,803 A | 9/1998 | Moss et al. |
| 5,810,804 A | 9/1998 | Gough et al. |
| 5,821,410 A | 10/1998 | Xiang et al. |
| 5,829,437 A | 11/1998 | Bridges |
| 5,861,021 A | 1/1999 | Thome et al. |
| 5,869,973 A | 2/1999 | Nosov |
| 5,900,618 A | 5/1999 | Anlage et al. |
| 5,902,251 A | 5/1999 | vanHooydonk |
| 5,904,709 A | 5/1999 | Arndt et al. |
| 5,921,982 A | 7/1999 | Lesh et al. |
| 5,957,969 A | 9/1999 | Warner et al. |
| 5,976,128 A | 11/1999 | Schilling et al. |
| 6,016,452 A | 1/2000 | Kasevich |
| 6,026,323 A | 2/2000 | Skladnev et al. |
| 6,026,331 A | 2/2000 | Feldberg et al. |
| 6,053,909 A | 4/2000 | Shadduck |
| 6,054,693 A | 4/2000 | Barmatz et al. |
| D424,694 S | 5/2000 | Tetzlaff et al. |
| D425,201 S | 5/2000 | Tetzlaff et al. |
| 6,059,780 A | 5/2000 | Gough et al. |
| 6,061,589 A | 5/2000 | Bridges et al. |
| 6,104,959 A | 8/2000 | Spertell |
| 6,109,268 A | 8/2000 | Thapliyal et al. |
| 6,112,123 A | 8/2000 | Kelleher et al. |
| 6,113,591 A | 9/2000 | Whayne et al. |
| 6,123,702 A | 9/2000 | Swanson et al. |
| 6,134,476 A | 10/2000 | Arndt et al. |
| 6,162,216 A | 12/2000 | Guzuak et al. |
| 6,175,768 B1 | 1/2001 | Arndt et al. |
| 6,179,832 B1 | 1/2001 | Jones et al. |
| 6,201,400 B1 | 3/2001 | Lind |
| 6,230,060 B1 | 5/2001 | Mawhinney |
| 6,231,569 B1 | 5/2001 | Bek et al. |
| 6,232,760 B1 | 5/2001 | Eckert |
| 6,233,479 B1 | 5/2001 | Haddad |
| 6,233,490 B1 | 5/2001 | Kasevich |
| 6,258,085 B1 | 7/2001 | Eggleston |
| 6,275,738 B1 | 8/2001 | Kasevich et al. |
| 6,293,941 B1 | 9/2001 | Strul et al. |
| D449,886 S | 10/2001 | Tetzlaff et al. |
| 6,309,386 B1 | 10/2001 | Bek |
| 6,370,426 B1 | 4/2002 | Campbell et al. |
| D457,958 S | 5/2002 | Dycus et al. |
| D457,959 S | 5/2002 | Tetzlaff et al. |
| 6,383,183 B1 | 5/2002 | Sekino et al. |
| 6,402,742 B1 | 6/2002 | Blewett et al. |
| 6,413,255 B1 | 7/2002 | Stern |
| 6,425,912 B1 | 7/2002 | Knowlton |
| 6,488,678 B2 | 12/2002 | Sherman |
| 6,496,738 B2 | 12/2002 | Carr |
| 6,524,308 B1 | 2/2003 | Muller et al. |
| 6,537,272 B2 | 3/2003 | Christopherson et al. |
| 6,546,292 B1 | 4/2003 | Steinhaus et al. |
| 6,577,903 B1 | 6/2003 | Cronin et al. |
| 6,597,185 B1 | 7/2003 | Talanov et al. |
| 6,610,054 B1 | 8/2003 | Edwards et al. |
| 6,629,974 B2 | 10/2003 | Penny et al. |
| 6,635,055 B1 | 10/2003 | Cronin |
| 6,648,883 B2 | 11/2003 | Francischelli et al. |
| 6,657,173 B2 | 12/2003 | Flugstad et al. |
| 6,677,762 B1 | 1/2004 | Adenot et al. |
| 6,690,976 B2 | 2/2004 | Fenn et al. |
| 6,692,492 B2 | 2/2004 | Simpson et al. |
| 6,725,095 B2 | 4/2004 | Fenn et al. |
| 6,730,079 B2 | 5/2004 | Lovewell |
| 6,768,925 B2 | 7/2004 | Fenn et al. |
| 6,784,405 B2 | 8/2004 | Flugstad et al. |
| 6,788,977 B2 | 9/2004 | Fenn et al. |
| D496,997 S | 10/2004 | Dycus et al. |
| 6,807,444 B2 | 10/2004 | Tu et al. |
| 6,807,446 B2 | 10/2004 | Fenn et al. |
| D499,181 S | 11/2004 | Dycus et al. |
| 6,813,515 B2 | 11/2004 | Hashimshony |
| 6,818,000 B2 | 11/2004 | Muller et al. |
| 6,849,073 B2 | 2/2005 | Hoey et al. |
| 6,850,804 B2 | 2/2005 | Eggers et al. |
| 6,866,624 B2 | 3/2005 | Chornenky et al. |
| 6,939,344 B2 | 9/2005 | Kreindel |
| 6,939,346 B2 | 9/2005 | Kannenberg et al. |
| 6,955,675 B2 | 10/2005 | Jain |
| 6,979,328 B2 | 12/2005 | Baerveldt et al. |
| 6,989,010 B2 | 1/2006 | Francischelli et al. |
| 6,993,394 B2 | 1/2006 | Eggers et al. |
| 7,001,415 B2 | 2/2006 | Hooven |
| 7,004,941 B2 | 2/2006 | Tvinnereim et al. |
| 7,048,756 B2 | 5/2006 | Eggers et al. |
| 7,056,011 B2 | 6/2006 | Pesach |
| D525,361 S | 7/2006 | Hushka |
| 7,074,217 B2 | 7/2006 | Strul et al. |
| 7,090,672 B2 | 8/2006 | Underwood et al. |
| D531,311 S | 10/2006 | Guerra et al. |
| D533,942 S | 12/2006 | Kerr et al. |
| 7,146,210 B2 | 12/2006 | Paiti |
| D535,027 S | 1/2007 | James et al. |
| 7,160,296 B2 | 1/2007 | Pearson et al. |
| 7,169,144 B2 | 1/2007 | Hoey et al. |
| 7,184,824 B2 | 2/2007 | Hashimshony |
| D541,418 S | 4/2007 | Schechter et al. |
| 7,207,989 B2 | 4/2007 | Pike, Jr. et al. |
| D541,938 S | 5/2007 | Kerr et al |
| 7,247,155 B2 | 7/2007 | Hoey et al. |
| 7,282,049 B2 | 10/2007 | Orszulak et al. |
| 7,294,127 B2 | 11/2007 | Leung et al. |
| 7,304,488 B2 | 12/2007 | Gleason et al. |
| 7,311,703 B2 | 12/2007 | Turovskiy et al. |
| 7,330,041 B2 | 2/2008 | McFadden |
| D564,662 S | 3/2008 | Moses et al. |
| 7,341,586 B2 | 3/2008 | Daniel et al. |
| 7,344,533 B2 | 3/2008 | Pearson et al. |
| 7,367,972 B2 | 5/2008 | Francischelli et al. |
| 7,393,352 B2 | 7/2008 | Berube |
| 7,410,485 B1 | 8/2008 | Fink et al. |
| 7,417,446 B2 | 8/2008 | Hayden et al. |
| 7,419,487 B2 | 9/2008 | Johnson et al. |
| 7,422,586 B2 | 9/2008 | Morris et al. |
| 7,449,899 B2 | 11/2008 | Campbell et al. |
| 7,452,358 B2 | 11/2008 | Stern et al. |
| 7,453,276 B2 | 11/2008 | Hayden et al. |
| 7,467,015 B2 | 12/2008 | van der Weide |
| 7,473,251 B2 | 1/2009 | Knowlton et al. |
| 7,479,141 B2 | 1/2009 | Kleen et al. |
| 7,483,755 B2 | 1/2009 | Ingle et al. |
| 2001/0001819 A1* | 5/2001 | Lee et al. .................... 606/41 |
| 2001/0008966 A1 | 7/2001 | Arndt et al. |
| 2001/0008967 A1 | 7/2001 | Sherman |
| 2002/0049483 A1 | 4/2002 | Knowlton |
| 2002/0058933 A1* | 5/2002 | Christopherson et al. ...... 606/34 |
| 2002/0087151 A1 | 7/2002 | Mody et al. |
| 2002/0091427 A1 | 7/2002 | Rappaport et al. |
| 2002/0128636 A1 | 9/2002 | Chin et al. |
| 2002/0135103 A1 | 9/2002 | Odorzynski et al. |
| 2002/0156471 A1 | 10/2002 | Stern et al. |
| 2003/0004454 A1 | 1/2003 | Fenn et al. |
| 2003/0050630 A1 | 3/2003 | Mody et al. |
| 2003/0050631 A1 | 3/2003 | Mody |
| 2003/0060818 A1 | 3/2003 | Kannenberg et al. |

(56) References Cited

U.S. PATENT DOCUMENTS

| | | |
|---|---|---|
| 2003/0069575 A1 | 4/2003 | Chin et al. |
| 2003/0069619 A1 | 4/2003 | Fenn et al. |
| 2003/0073989 A1 | 4/2003 | Hoey et al. |
| 2003/0083654 A1 | 5/2003 | Chin et al. |
| 2003/0097162 A1 | 5/2003 | Kreindel |
| 2003/0109778 A1 | 6/2003 | Rashidi |
| 2003/0109868 A1 | 6/2003 | Chin et al. |
| 2003/0130711 A1 | 7/2003 | Pearson et al. |
| 2003/0163128 A1 | 8/2003 | Patil et al. |
| 2003/0187366 A1 | 10/2003 | Hashimshony |
| 2003/0212394 A1 | 11/2003 | Pearson et al. |
| 2004/0049251 A1 | 3/2004 | Knowlton |
| 2004/0078036 A1* | 4/2004 | Keidar ............................ 606/41 |
| 2004/0122494 A1 | 6/2004 | Eggers et al. |
| 2004/0138652 A1 | 7/2004 | Berube |
| 2004/0138653 A1 | 7/2004 | Dabney et al. |
| 2004/0230263 A1 | 11/2004 | Samulski |
| 2005/0015081 A1 | 1/2005 | Turovskiy et al. |
| 2005/0033278 A1 | 2/2005 | McClurken et al. |
| 2005/0137662 A1 | 6/2005 | Morris et al. |
| 2006/0015162 A1 | 1/2006 | Edward et al. |
| 2006/0020312 A1 | 1/2006 | Eggers et al. |
| 2006/0020313 A1 | 1/2006 | Eggers et al. |
| 2006/0030912 A1 | 2/2006 | Eggers et al. |
| 2006/0030913 A1 | 2/2006 | Eggers et al. |
| 2006/0030914 A1 | 2/2006 | Eggers et al. |
| 2006/0217694 A1 | 9/2006 | Chin et al. |
| 2007/0050001 A1 | 3/2007 | Luttich et al. |
| 2007/0056960 A1 | 3/2007 | Bell |
| 2007/0078454 A1 | 4/2007 | McPherson |
| 2007/0088413 A1 | 4/2007 | Weber et al. |
| 2007/0093800 A1 | 4/2007 | Wham et al. |
| 2007/0106349 A1 | 5/2007 | Karni et al. |
| 2007/0135700 A1 | 6/2007 | Taimisto et al. |
| 2007/0142829 A1 | 6/2007 | Ahn et al. |
| 2007/0156211 A1 | 7/2007 | Ferren et al. |
| 2007/0185554 A1 | 8/2007 | Appling et al. |
| 2007/0191825 A1 | 8/2007 | Cronin et al. |
| 2007/0198006 A1 | 8/2007 | Prakash et al. |
| 2007/0203551 A1 | 8/2007 | Cronin et al. |
| 2007/0225697 A1 | 9/2007 | Shroff et al. |
| 2007/0233057 A1 | 10/2007 | Knishi et al. |
| 2007/0250051 A1 | 10/2007 | Gaston et al. |
| 2007/0265606 A1 | 11/2007 | DeBenedictis et al. |
| 2007/0270924 A1 | 11/2007 | McCann et al. |
| 2007/0284034 A1 | 12/2007 | Fathi et al. |
| 2007/0296435 A1 | 12/2007 | Eldridge et al. |
| 2007/0299488 A1 | 12/2007 | Carr |
| 2008/0015571 A1 | 1/2008 | Rubinsky et al. |
| 2008/0033417 A1 | 2/2008 | Nield et al. |
| 2008/0033418 A1 | 2/2008 | Nields et al. |
| 2008/0033419 A1 | 2/2008 | Nields et al. |
| 2008/0033420 A1 | 2/2008 | Nields et al. |
| 2008/0033422 A1 | 2/2008 | Turner et al. |
| 2008/0058793 A1 | 3/2008 | Pilla et al. |
| 2008/0061055 A1 | 3/2008 | Moriya et al. |
| 2008/0065059 A1 | 3/2008 | Lukowiak et al. |
| 2008/0082093 A1 | 4/2008 | Prakash et al. |
| 2008/0097558 A1 | 4/2008 | Eggers et al. |
| 2008/0097559 A1 | 4/2008 | Eggers et al. |
| 2008/0108985 A1 | 5/2008 | Konesky |
| 2008/0140062 A1 | 6/2008 | Cronin |
| 2008/0147056 A1 | 6/2008 | van der Weide et al. |
| 2008/0149623 A1 | 6/2008 | Givens |
| 2008/0183165 A1 | 7/2008 | Buyasse |
| 2008/0183251 A1 | 7/2008 | Azar et al. |
| 2008/0200969 A1 | 8/2008 | Weber |
| 2008/0221650 A1 | 9/2008 | Turner et al. |
| 2008/0228062 A1 | 9/2008 | Zwirn et al. |
| 2008/0234574 A1 | 9/2008 | Hancock et al. |
| 2008/0249530 A1 | 10/2008 | Truckai et al. |
| 2008/0255570 A1 | 10/2008 | Truckai et al. |
| 2008/0255571 A1 | 10/2008 | Truckai et al. |
| 2008/0269851 A1 | 10/2008 | Deem et al. |
| 2008/0275436 A1 | 11/2008 | Cronin et al. |
| 2008/0294155 A1 | 11/2008 | Cronin |
| 2008/0312651 A1 | 12/2008 | Pope et al. |
| 2008/0319434 A1 | 12/2008 | Rick et al. |
| 2008/0319437 A1 | 12/2008 | Turner et al. |
| 2009/0030312 A1 | 1/2009 | Hadjicostis |
| 2009/0054884 A1 | 2/2009 | Farley et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 519 415 | 6/1992 |
| EP | 0 521 264 | 1/1993 |
| EP | 0 556 705 | 8/1993 |
| EP | 0 558 429 | 9/1993 |
| EP | 0 694 291 | 1/1996 |
| EP | 0 836 868 | 4/1998 |
| EP | 0 882 955 | 12/1998 |
| EP | 1 051 949 | 11/2000 |
| EP | 1 159 926 | 5/2001 |
| EP | 1 645 236 | 4/2006 |
| EP | 1 810 627 | 7/2009 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |

(56) References Cited

FOREIGN PATENT DOCUMENTS

| JP | 11244298 | 9/1999 |
|---|---|---|
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | 00/51513 | 9/2000 |
| WO | 00/54682 | 9/2000 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences• Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Christopher L. Brace, "Temperature-Dependent Dielectric Properties of Liver Tissue Measured During Thermal Ablation: Toward an Improved Numerical Model" 2008 IEEE pp. 230-233.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.

(56) References Cited

OTHER PUBLICATIONS

European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCTTUS01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

BIPOLAR ELECTRODE PROBE FOR ABLATION MONITORING

BACKGROUND

1. Technical Field

The present disclosure relates to systems and methods for providing energy to biological tissue and, more particularly, to apparatus and methods for sensing one or more properties of tissue at one or more locations during a microwave ablation procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna tuning, antenna impedance and tissue impedance. Tissue impedance may change during an ablation procedure due to a number of factors, e.g., tissue denaturization or desiccation occurring from the absorption of microwave energy by tissue. Changes in tissue impedance may cause an impedance mismatch between the probe and tissue, which may affect delivery of microwave ablation energy to targeted tissue. The temperature and/or impedance of targeted tissue, and of non-targeted tissue and adjacent anatomical structures, may change at varying rates which may be greater, or less than, expected rates. A surgeon may need to perform an ablation procedure in an incremental fashion in order to avoid exposing targeted tissue and/or adjacent tissue to excessive temperatures and/or denaturation. In certain circumstances, a surgeon may need to rely on experience and/or published ablation probe parameters to determine an appropriate ablation protocol (e.g., ablation time, ablation power level, and the like) for a particular patient.

SUMMARY

The present disclosure is directed to an electromagnetic surgical ablation system that includes one or more tissue sensor probes adapted to sense a tissue property, e.g., tissue impedance, at or near an ablation surgical site. Also disclosed is a controller module which may include a sensor interface having one or more sensor inputs adapted to receive a sensor signal from the one or more tissue sensor probes. Additionally or alternatively, one or more sensor interfaces may be provided by the controller module. The disclosed sensor interface may include an impedance measurement circuit that is adapted to perform a conversion of a raw signal, which may be received from the one or more tissue sensor probes, into an impedance measurement suitable for processing by a processor included within the controller.

The disclosed surgical ablation system may include a source of microwave ablation energy, such as a generator, that is responsive to a control signal generated by the control module. The one or more tissue sensor probes, the controller, and the generator function cooperatively to enable a surgeon to monitor one or more tissue properties at, or adjacent to, an ablation surgical site. Additionally or alternatively, the described arrangement may enable the automatic control, activation, and/or deactivation of ablative energy applied to tissue to enable precise control over the ablation size and/or volume created during an ablation procedure.

In addition, the present disclosure provides an electromagnetic surgical ablation system having a generator adapted to selectively provide surgical ablative energy to an ablation probe. The ablation probe is operably coupled to the generator and adapted to receive ablative energy therefrom, and to deliver said ablative energy to targeted tissue, e.g., a tumor, polyp, or necrotic lesion. The disclosed system includes a controller operatively coupled to the generator, the controller including at least one processor, a memory operatively coupled to the processor, a sensor interface circuit operatively coupled to the processor and adapted to receive one or more impedance sensor signals from one or more tissue sensor probes. Additionally or alternatively, a tissue sensor probe may include additional sensors, such as without limitation, a temperature sensor. In such an embodiment, the sensor interface circuit may include a temperature sensor circuit operatively coupled to the processor and adapted to receive a temperature sensor signal from a tissue sensor probe.

In one aspect, a system in accordance with the present disclosure may enable a surgeon to place one or more tissue sensor probes around a targeted ablation region, and/or between a targeted ablation region and an adjacent anatomical structure. During an ablation procedure, the controller may monitor the one or more sensors to track the progress of the ablation region as tissue is "cooked", based at least in part upon an impedance change detected at the one or more probe locations. In an embodiment, a feedback signal may be provided to the surgeon, e.g., a visual, audible, and/or tactile indication, such that a surgeon may follow the ablation region formation in real-time or in near-real-time. Each probe may be positioned such that targeted tissue may be monitored at various locations around, and/or distances from, an ablation probe being utilized to deliver ablative energy to tissue.

A tissue sensor probe may be identified (e.g., assigned or tagged) and/or adapted as a "threshold" probe or a "critical structure" tag. It is envisioned that a threshold tag may be configured to sense when the tissue associated therewith has reached an ablation threshold, e.g., the point at which the desired degree of desiccation has occurred. As tissue associated with a given probe has reached the desired ablation state, an indicator associated with the sensor may be activated. When a plurality of threshold probes are utilized, a surgeon may recognize when an ablation procedure is completed by noting when all, or a sufficient number of, indicators associated with the various probes have been activated. In an embodiment, the controller may automatically deactivate a generator when all, or a sufficient number of, threshold probes have reached a predetermined threshold.

A probe identified as a "critical structure" probe may be configured to activate an indicator, which may be an alarm indicator, when tissue associated therewith is about to, but has not yet, received ablative energy in excess of a predetermined safety threshold. Additionally or alternatively, the disclosed system may be configured to automatically deactivate a generator when a predetermined number (e.g., one or more) of indicators associated with a critical structure probe have been activated. While it is contemplated that a critical structure probe may be positioned between an operative field and an adjacent critical anatomical structure, it should be understood that the present disclosure is in no way limited to such use and that the described probes and features may be advantageously utilized in any combination for any purpose.

Also disclosed is a method of operating an electromagnetic surgical ablation system. The disclosed method includes the steps of activating an electrosurgical generator to deliver ablative energy to tissue and sensing a tissue impedance parameter from at least one tissue sensing probe, which may be inserted into tissue. A determination is made as to whether a sensed tissue impedance parameter exceeds a predetermined tissue impedance parameter threshold. In response to a determination that a sensed tissue impedance parameter exceeds a predetermined tissue impedance parameter threshold, an action is performed, e.g., the electrosurgical generator is deactivated and/or an indication is presented.

The present disclosure also provides a computer-readable medium storing a set of programmable instructions configured for being executed by at least one processor for performing a method of performing microwave tissue ablation in response to monitored tissue temperature and/or monitored tissue dielectric properties in accordance with the present disclosure.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
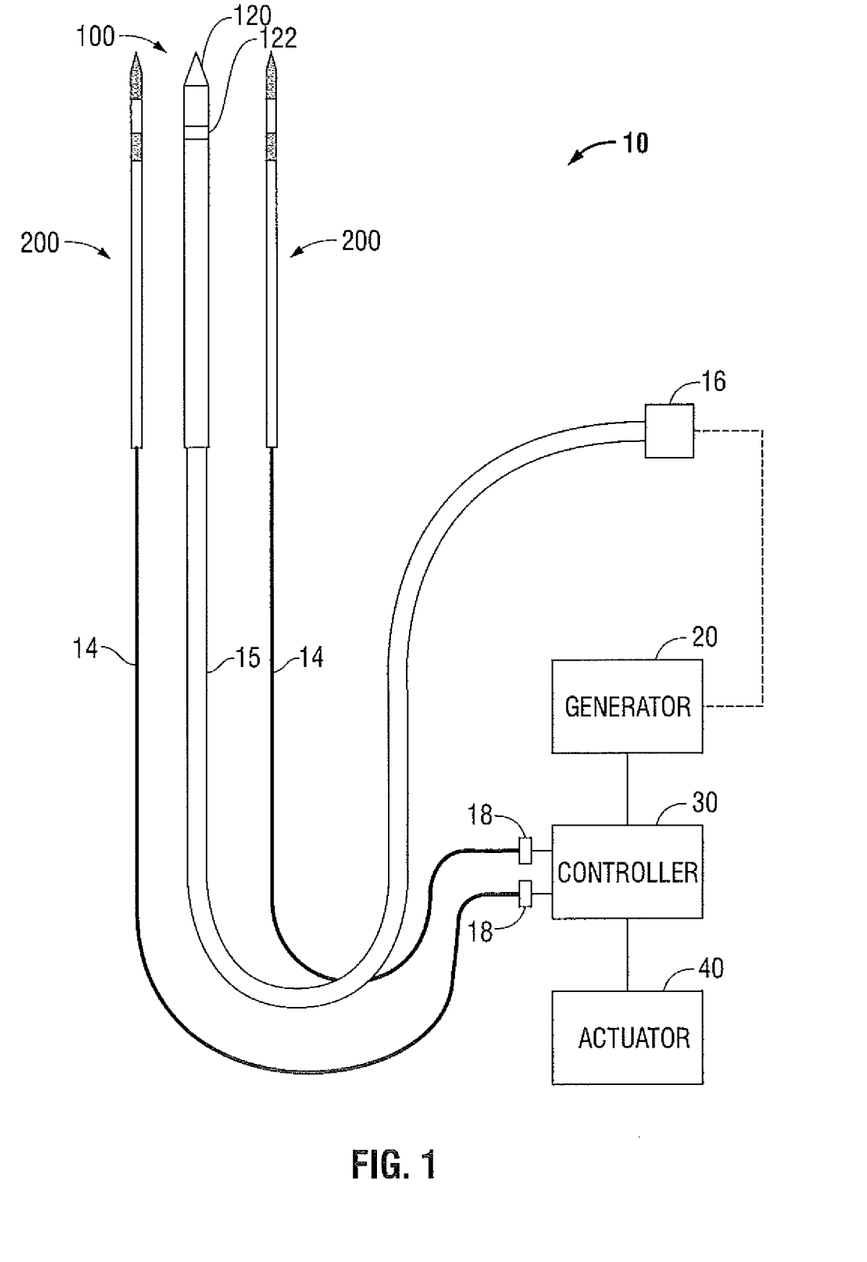
FIG. 1 shows a diagram of a microwave ablation system having an electromagnetic surgical ablation probe and at least one tissue sensor probe in accordance with the present disclosure.

FIG. 1 shows an embodiment of a microwave ablation system 10 in accordance with the present disclosure. The microwave ablation system 10 includes an electromagnetic surgical ablation probe 100 having a having-a tapered distal tip 120 and a feed point 122. The ablation probe 100 is operably connected by a cable 15 to connector 16, which further operably connects probe 100 to a generator assembly 20. Generator assembly 20 may be a source of ablative energy, e.g., microwave or RF energy in the range of about 915 MHz to about 10 GHz. The disclosed system 10 includes one or more tissue sensor probes 200 that are adapted to sense one or more operative parameters, e.g., a tissue impedance. The tissue sensor probe 200 is operably connected by a cable 14 to a connector 18, which further operably connects tissue sensor probe 200 to a controller assembly 30. An actuator 40 is operably coupled to the controller to enable a user, e.g., a surgeon, to selectively activate and de-activate the delivery of ablative energy to patient tissue. Controller 30 is operably coupled to generator 20 to enable communication therebetween, such as without limitation, a control signal and/or a status signal.

Figure 2:
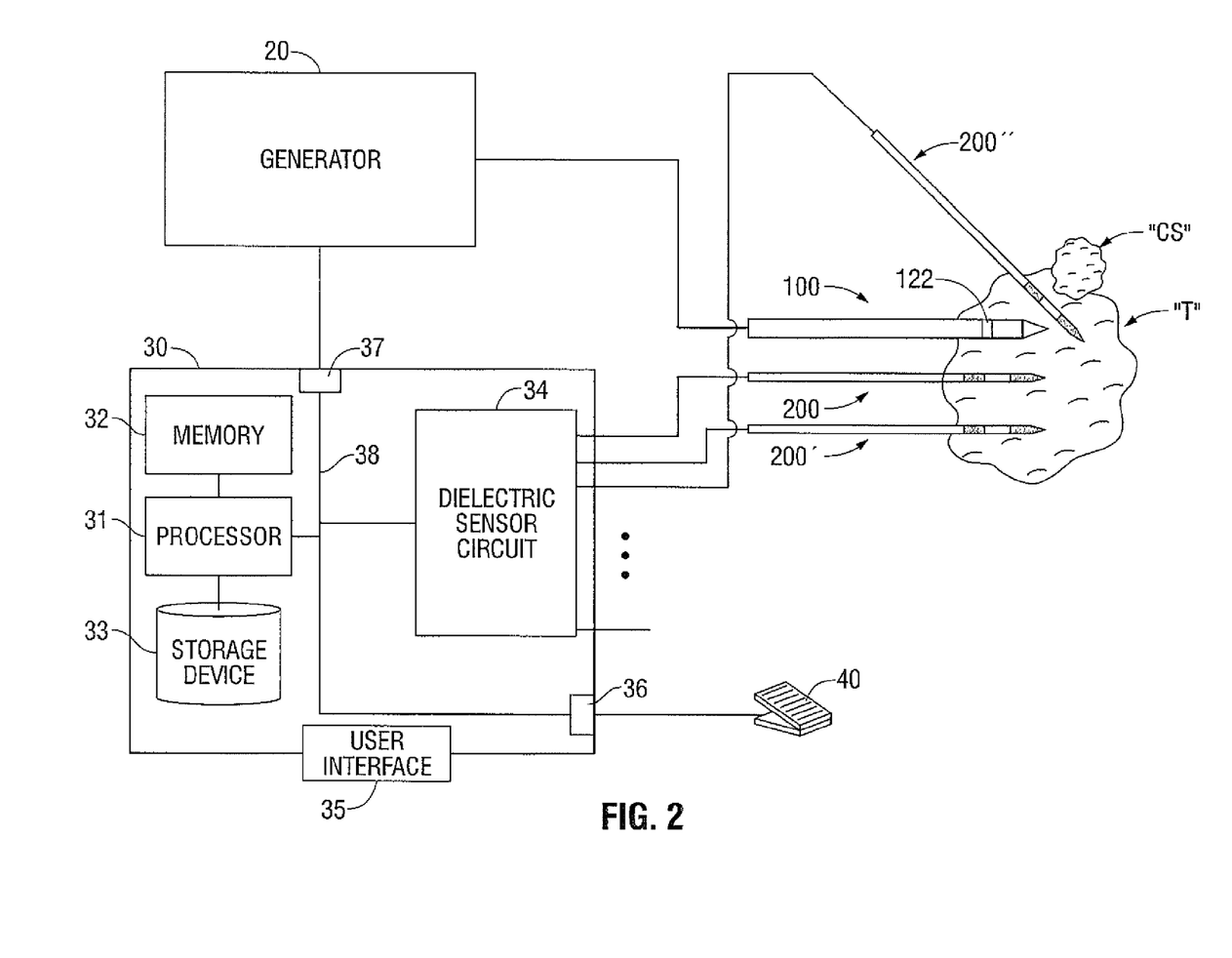
FIG. 2 shows a block diagram of a microwave ablation system having an electromagnetic surgical ablation probe and at least one tissue sensor probe in accordance with the present disclosure.

In more detail, FIG. 2 illustrates a functional block diagram of an ablation system 10 in accordance with the present disclosure. The system 10 includes a controller 30 that includes one or more processors 31 operatively coupled to memory 32, storage device 33, sensor interface 34, and user interface 35. Processor 31 is configured to execute a set of programmed instructions for performing a method of microwave ablation as disclosed herein. Memory 32 and/or storage device 33 may include any suitable memory device, including without limitation, semiconductor memory (e.g., random-access memory, read-only memory, flash memory), hard disk, optical storage (e.g., CD-ROM, DVD-RAM, etc.), USB memory stick, and the like.

Controller 30 includes an actuator interface 36 that is adapted to facilitate operative coupling with actuator 40 and/or a generator interface 37 that is adapted to facilitate operative coupling with generator 20. Actuator 40 may be any suitable actuator, such as without limitation, a footswitch, a handswitch (which may be mounted on a probe 100 and/or a tissue sensor probe 200), an orally-activated switch (e.g., a bite-activated switch and/or a breath-actuated switch), and the like. The processor 31, memory 32, storage device 33, sensor interface 34, actuator interface 36 and/or generator interface 37 may be separate components or may be integrated, such as in one or more integrated circuits. The various components in the controller 30 are coupled by one or more communication buses or signal lines 38. Memory 30 and/or storage device 33 may include a set of executable instructions for performing a method of microwave ablation as described herein. One or more elements of ablation system 10 may be coupled using a hard-wired connection (e.g., copper wire and/or fiber optic media) and/or a wireless link. During use, the one or more tissue sensor probe 200 may be positioned in tissue T in proximity to probe 100 to obtain one or more tissue parameter(s), e.g., tissue impedance.

User interface 35 may include any suitable form of visual, audible, or tactile user interface elements, including without limitation, a graphic display panel (e.g., LCD, LED, OLED plasma, gas-discharge display, and the like), touchscreen, keypad, pushbutton, switch, lamp, annunciator, speaker, haptic feedback device, and so forth.

As shown in FIG. 2, and by way of example only, an ablation probe 100 is inserted into tissue T for use. A tissue sensor probe 200 is inserted into tissue T in a position generally adjacent to probe 200. Another tissue sensor probe 200' is inserted into tissue T at a position further from probe 100. Yet a third tissue sensor probe 200" is inserted into tissue T at a position generally between probe 100 and a critical anatomical structure CS. During use, ablative energy from probe 100 is delivered into tissue T to effectuate ablation of at least a part of tissue T. Denaturation of tissue T proceeds generally outwardly from feed point 122. As the volume of denatured (ablated) tissue expands, an impedance boundary expands in a corresponding manner.

It has been observed that during an initial phase of an ablation procedure, tissue impedance will remain relatively constant. As tissue approaches denaturation (e.g., as tissue becomes "cooked"), impedance tends to rise rapidly. By sensing the impedance at one or more points surrounding the ablation probe 100, the formation of the ablated volume of tissue may be accurately monitored. In turn, the delivery of ablative energy may be controlled in response to the one or more impedance measurements obtained from the surrounding tissue. Thus, a surgeon may define a desired ablation region by deliberately positioning one or more tissue sensor probes 200 at or near the outer boundaries of the desired region. As each probe 200 senses a rise in impedance (which may signify tissue denaturation has occurred), a corresponding indication may be presented to a user (e.g., a surgeon) that ablation of the tissue corresponding to the probe has completed. An indication may be presented via user interface 35. The defined ablation volume is deemed fully ablated once each designated tissue probe 200 has sensed an impedance rise corresponding to denaturation. An "ablation complete" indication may then be presented to the user, or, additionally or alternatively, the generator 20 may be automatically deactivated. In this manner, the ablation region may be precisely controlled with greatly reduced risk of over-ablation and/or excessive charring of tissue or injuring critical structures.

The tissue probe(s) 200 may be designated as a threshold probe or a critical structure probe. One or more threshold probes may be used to define an ablation volume by deliberate placement in tissue by a surgeon, as described hereinabove. The one or more threshold probe(s) may be grouped to define a threshold group, whereby an ablation complete status is established when each threshold probe in a group has sensed an impedance rise corresponding to tissue denaturation. In contrast, a critical structure probe may be used to recognize a pre-denaturation state of tissue, such as without limitation, an initial slight or gradual rise in impedance which may precede a more pronounced or rapid rise in impedance associated with tissue denaturation. In an embodiment, if any one critical structure probe senses pre-denaturation, an indicator may be presented to the user and/or generator 20 deactivated. In this manner, undesired ablation of one or more critical anatomical structures at or near the ablation site may be prevented.

Figure 6:
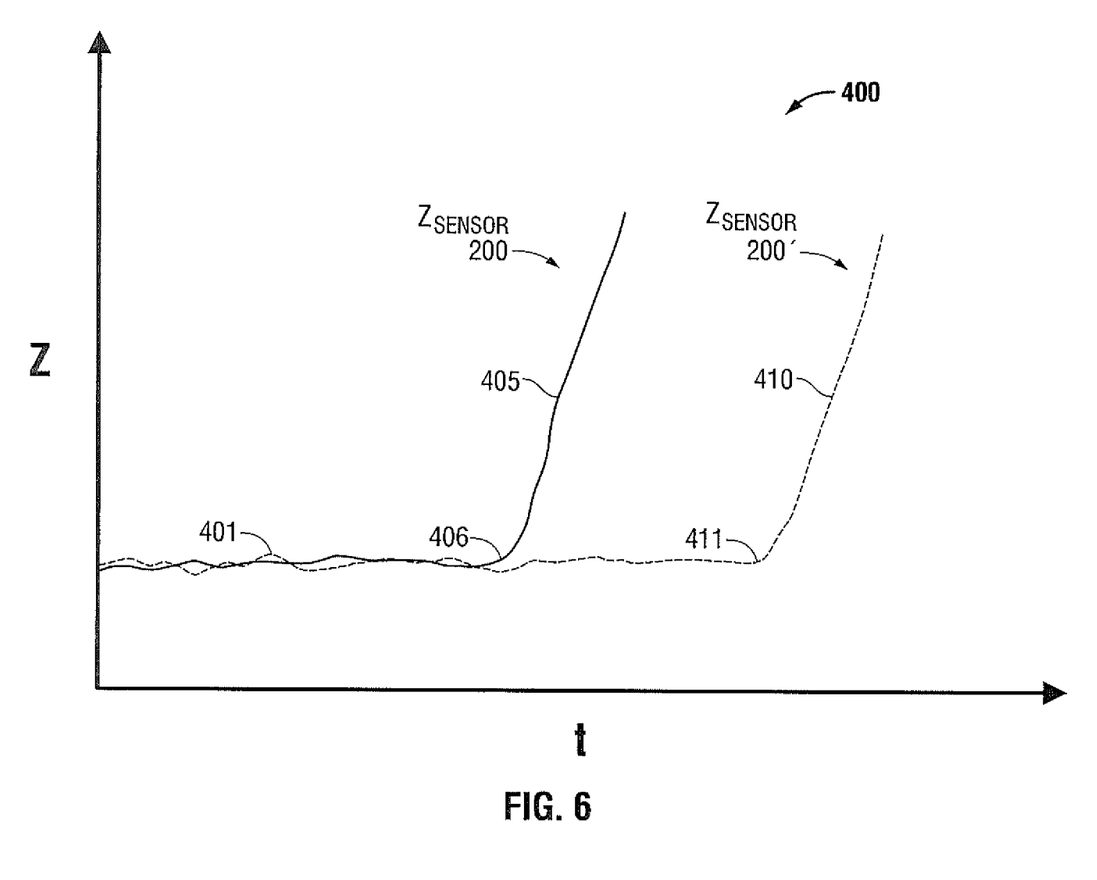
FIG. 6 illustrates a relationship between time, an impedance sensed by a first tissue sensor probe, and an impedance sensed by a second tissue sensor probe in accordance with the present disclosure.

A graph illustrating a relationship between sensor position, ablation time, and tissue impedance (shown generally as 400) is presented in FIG. 6, wherein a first impedance curve 405 corresponding to a first tissue sensor probe 200, and a second impedance curve 410 corresponding to a second tissue sensor probe 200', are shown. Initially, as ablation energy is first delivered to tissue, both tissue sensor probes 200 and 200' indicate a relatively constant impedance value 401. As ablation time t progresses, tissue surrounding first tissue sensor probe 200 begins to denature, as illustrated by a rise in impedance 406. As ablation continues, the volume of denatured tissue expands, and eventually, reaches second tissue sensor probe 200', as illustrated by a second rise in impedance 411. Denaturation may be indicated by, e.g., an absolute rise in impedance, a change in impedance from an initial impedance value, and/or rate of change of impedance exceeding a predetermined rate.

Designation of a tissue probe 200 as a threshold probe or a critical structure probe may be accomplished manually by, e.g., a user entering the appropriate designation via user interface 35. Additionally or alternatively, a tissue probe 200 may include an identifier (not explicitly shown) that identifies to controller 30 the probe as a threshold probe, a critical structure probe, or a universal probe which may function as either a threshold probe or a critical structure probe. The identifier may include, without limitation, an RFID tag, a semiconductor memory device (e.g., ROM, EEPROM, NAND or NOR flash memory), an encoded electrical component (encoded resistor value), a mechanical identifier (e.g., physically encoded connector member), an optical identifier (e.g., a barcode) and the like. In an embodiment, a user entry may override an identifier-defined designation of a probe 200.

Figure 3:
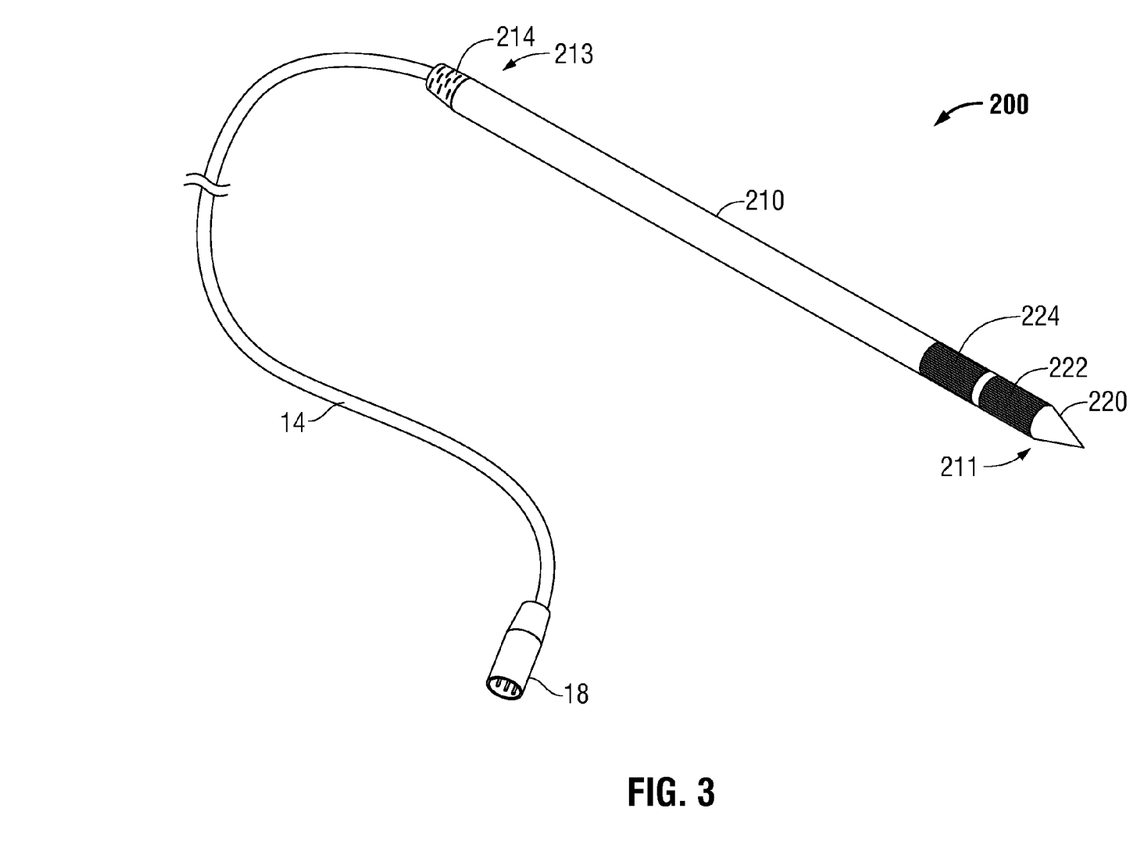
FIG. 3 is a perspective view of a tissue sensor probe in accordance with the present disclosure.
Figure 4:
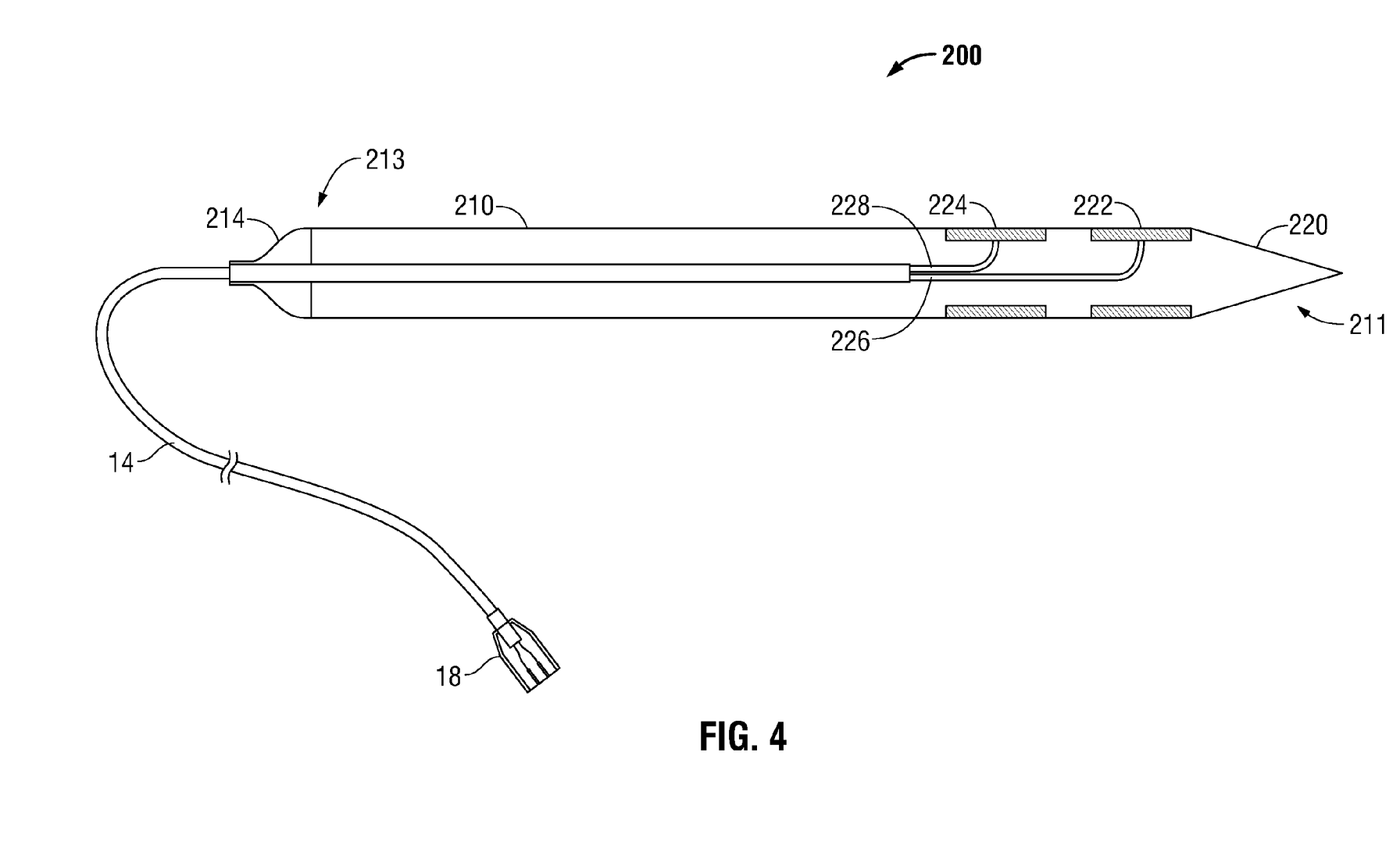
FIG. 4 is a side, cutaway view of a tissue sensor probe in accordance with the present disclosure.

A tissue sensor probe 200 in accordance with an embodiment of the present disclosure is now described with reference to FIGS. 3 and 4. The disclosed tissue sensor probe 200 includes an elongated shaft 210 having a proximal end 213 and a distal end 211. A tapered tip 220 may be disposed at a distal end 211 of the probe 200 to facilitate the insertion of probe 200 into tissue. As shown, tapered tip 220 has a generally conical shape; however, any suitable tip shape may be utilized. A pair of electrodes 222, 224 are disposed on an exterior portion of the shaft 210. As shown, electrodes 222, 224 are substantially annular in shape and disposed coaxially about the shaft 210; however, other electrode arrangements are contemplated within the scope of the present invention, including without limitation, longitudinal electrodes, helical electrodes, dot-shapes electrodes, and so forth. Electrodes 222, 224 may be formed from any suitable biocompatible and electrically conductive material, such as without limitation, stainless steel. In an embodiment, electrodes 222, 224 are disposed generally toward a distal end 211 of the shaft 210; however, it is to be understood that either or both electrodes 222, 224 may be positioned at other locations along shaft 210.

The probe 200 includes a pair of conductors 226, 228 that are configured to place electrodes 222, 224, respectively, in electrical communication with controller 30 via cable 14 and/or connector 18. A distal end of conductor 226 is electrically coupled to electrode 222. A distal end of conductor 228 is electrically coupled to electrode 224. The connection between conductors 226, 228 to electrodes 222, 224, respectively, may be formed by any suitable manner of electrical or electromechanical connection, including without limitation soldering, brazing, welding, crimping, and/or threaded coupling. Cable 14 extends from a proximal end 213 of shaft 210, and may be supported by a strain relief 214.

Shaft 210 and electrodes 222, 224 may be formed by any suitable manner of manufacture. In an embodiment, shaft 210 may be formed by injection overmolding. By way of example only, shaft 210 may be formed from a high strength, electrically insulating material, e.g., fiber-reinforced polymer, fiberglass resin composite, long strand glass-filled nylon, and the like. During use, probe 200 may be inserted into tissue, placing electrodes 222, 244 into electrical communication with tissue thereby enabling sensor interface 34, and controller 30 generally, to obtain an impedance measurement thereof.

Figure 5:
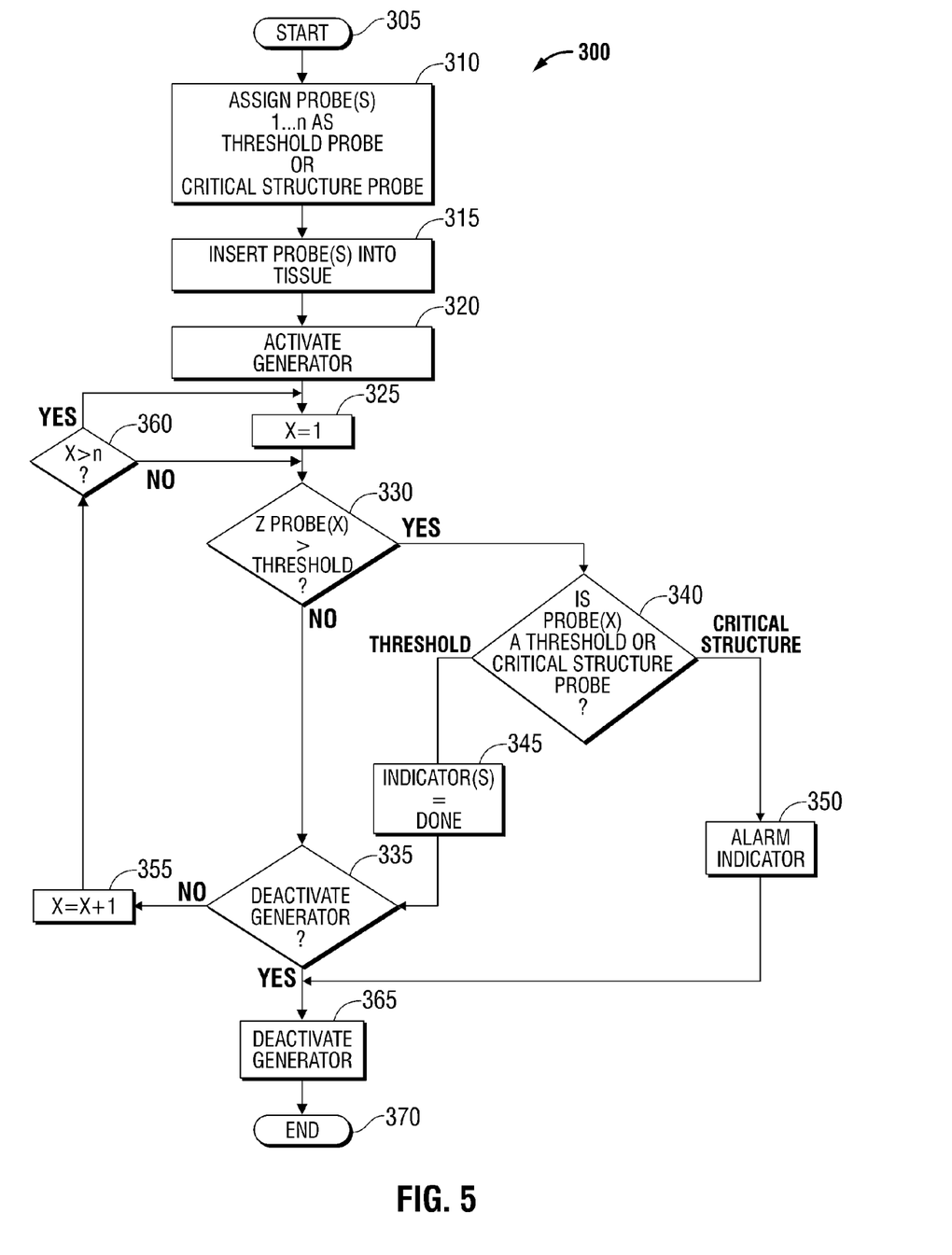
FIG. 5 is a flowchart showing a method of operation of a microwave ablation system having one or more tissue sensor probes in accordance with the present disclosure.

Turning to FIG. 5, a method 300 of operating an electromagnetic surgical ablation system having an ablation probe 100, and one or more tissue sensor probe(s) 200, is shown. The disclosed method begins in step 305 wherein one or more initializations may be performed, e.g., power-on self test (POST), memory allocation, input/output (I/O) initialization, and the like. In step 310, each of the tissue sensor probes to be used in the ablation procedure is designated as a threshold probe or a critical structure probe. In an embodiment, the user (e.g., a surgeon or an assisting practitioner) may manually input a corresponding designation for each tissue sensor probe. Additionally or alternatively, the tissue sensor probe may be automatically identified by an identifier included within the probe 200 and sensed by controller 30 and/or sensor interface 34 as described hereinabove.

A threshold value for each tissue sensor probe 200 may be established. In one embodiment, a threshold value for a threshold tissue sensor may differ from a threshold value for a critical structure tissue sensor. A threshold may be an absolute threshold, e.g., exceeding a fixed impedance value; a relative threshold, e.g., exceeding a predetermined change in impedance; or a rate threshold, e.g., where the rate of impedance change exceeds a predetermined rate. Other thresholds are contemplated within the scope of the present disclosure, including without limitation, spectral-based thresholds, wavelet-based thresholds, and impedance contour recognition thresholds.

The total number of tissue sensor probes designated for use during an ablation procedure may be represented as n. In step 315, the one or more tissue sensor probes are inserted into tissue in accordance with surgical requirements. In particular, a threshold probe is placed at or near an outer boundary of the desired ablation region, while a critical structure probe is positioned between the intended ablation region and a critical anatomical structure to be protected. In addition, an ablation probe 100 is positioned or inserted into tissue, e.g., the ablation site.

Once the ablation probe 100 and the one or more tissue sensor probes 200 have been positioned, the generator 20 is activated in step 320 to cause electromagnetic energy to be delivered to tissue. Generally, activation of generator 20 will be effectuated in response to engagement of actuator 40. During the ablative energy delivery process, the impedance of each designated tissue sensor probe is monitored. In step 325 a monitoring loop is established wherein a tissue sensor probe counter x is initialized, e.g., set to address the first of the currently-utilized one or more tissue sensor probes 200, which may be expressed as probe(x). In step 330, an impedance value of the currently-addressed tissue sensor probe 200, which may be expressed as Zprobe(x), is compared to a corresponding threshold value. If Zprobe(x) does not exceed a corresponding threshold value, the method proceeds to step 335 wherein it is determined whether the generator is to be deactivated, e.g., the user has released actuator 40. If, in step 335, it is determined that the generator 20 is to be deactivated, in step 365 the generator is deactivated and the process concludes with step 370.

If, in step 335, it is determined that the generator 20 is to remain activated, in step 355 the tissue sensor probe counter x is incremented to address the next tissue sensor probe in use and, in step 360, the tissue sensor probe counter is compared to the total number of tissue sensor probes designated for use. If, in step 360, it is determined that the tissue sensor probe counter exceeds the total number of tissue sensor probes designated for use, the tissue sensor probe counter x is re-initialized in step 325; otherwise, the method continues with step 330 wherein the impedance value of a subsequent tissue sensor probe 200 is evaluated.

If, in step 330, it is determined that Zprobe(x) exceeds a corresponding threshold value, then in step 340 it is determined whether the currently-addressed tissue sensor probe, i.e., probe(x), is designated as a threshold probe or a critical structure probe. If probe(x) is a critical structure probe, then in step 350 an alarm indication is presented to the user, and step 365 is performed wherein the generator 20 is deactivated, which may help reduce possible damage to the critical structure corresponding to probe(x). If probe(x) is a threshold probe, then a status indication is presented to the user in step 345 (to indicate ablation progress status) and the method proceeds to step 335 as described hereinabove. In an embodiment, an additional test may be performed wherein it is determined whether all threshold probes currently in use, and/or all threshold probes within a designated probe group, have exceeded the corresponding threshold thereof, and, if so, continue with step 365 to deactivate generator 20.

It is to be understood that the steps of the method provided herein may be performed in combination and/or in a different order than presented herein without departing from the scope and spirit of the present disclosure.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law. The claims can encompass embodiments in hardware, software, firmware, microcode, or a combination thereof.

What is claimed is:

1. A method of operating an ablation system, comprising the steps of:
    activating a generator to deliver ablative energy to tissue;
    sensing a tissue impedance parameter from each of a plurality of tissue sensing probes;
    designating each of the plurality of tissue sensing probes as a threshold probe or a critical structure probe;
    determining whether the sensed tissue impedance parameter from each of the plurality of tissue sensing probes exceeds a predetermined tissue impedance parameter threshold, wherein, for each of the plurality of tissue sensing probes designated as a critical structure probe, the predetermined tissue impedance parameter threshold is indicative of a pre-denaturation state of tissue and, for each of the plurality of tissue sensing probes designated as a threshold probe, the predetermined tissue impedance parameter threshold is indicative of a denaturation state of tissue; and
    responding to a determination that the sensed tissue impedance parameter exceeds the predetermined tissue impedance parameter threshold by causing to be performed an action selected from the group consisting of automatically deactivating the generator and presenting an indication.

2. The method of operating an ablation system in accordance with claim 1, wherein the designation is performed in accordance with an identifier included in each of the plurality of tissue sensing probes.

3. The method of operating an ablation system in accordance with claim 2, further comprising the step of overriding the designation.

4. The method of operating an ablation system in accordance with claim 1, wherein the tissue impedance parameter threshold is selected from the group consisting of an absolute impedance value, a relative impedance value, and a rate of change of impedance value.

5. The method of operating an ablation system in accordance with claim 1, further comprising the step of deactivating the generator in response to a deactivation signal received from a user-actuatable device operably coupled to the generator.

6. The method of operating an ablation system in accordance with claim 1, wherein the predetermined tissue impedance parameter threshold indicative of a pre-denaturation state of tissue is an initial slight or gradual rise in impedance.

7. The method of operating an ablation system in accordance with claim 1, wherein the predetermined tissue impedance parameter threshold indicative of a denaturation state of tissue is a rate of change of impedance exceeding a predetermined rate.

8. A non-transitory computer-readable medium storing a set of instructions configured for being executed by at least one processor for performing a method for operating an electromagnetic surgical ablation system, comprising:
    activating a generator to deliver ablative energy to tissue;
    sensing a tissue impedance parameter from each of a plurality of tissue sensing probes;
    designating each of the plurality of tissue sensing probes as a threshold probe or a critical structure probe;
    determining whether the sensed tissue impedance parameter from each of the plurality of tissue sensing probes exceeds a predetermined tissue impedance parameter threshold, wherein, for each of the plurality of tissue sensing probes designated as a critical structure probe, the predetermined tissue impedance parameter threshold is indicative of a pre-denaturation state of tissue and, for each of the plurality of tissue sensing probes designated as a threshold probe, the predetermined tissue impedance parameter threshold is indicative of a denaturation state of tissue; and
    responding to a determination that the sensed tissue impedance parameter exceeds the predetermined tissue impedance parameter threshold by causing to be performed an action selected from the group consisting of automatically deactivating the generator and presenting an indication.

9. The non-transitory computer-readable medium in accordance with claim 8, wherein the designation is performed in accordance with an identifier included in each of the plurality of tissue sensing probes.

10. The non-transitory computer-readable medium in accordance with claim 8, the method further comprising the step of overriding the designation.

11. The non-transitory computer-readable medium in accordance with claim 8, wherein the tissue impedance parameter threshold is selected from the group consisting of an absolute impedance value, a relative impedance value, and a rate of change of impedance value.

* * * * *